United States Patent [19]

Buysch et al.

[11] Patent Number: 5,495,038
[45] Date of Patent: Feb. 27, 1996

[54] PROCESS FOR THE PURIFICATION OF DIPHENYL CARBONATE

[75] Inventors: Hans-Josef Buysch, Krefeld; Christine Mendoza-Frohn, Erkrath; Johann Rechner, Krefeld; Norbert Schön, Darmstadt, all of Germany

[73] Assignee: Bayer Aktiengesellschaft, Leverkusen, Germany

[21] Appl. No.: 465,135

[22] Filed: Jun. 5, 1995

[30] Foreign Application Priority Data

Jun. 15, 1994 [DE] Germany ............ 44 20 778.6

[51] Int. Cl.⁶ .................................. C07C 68/08
[52] U.S. Cl. ................................... 558/274
[58] Field of Search ............................ 558/274

[56] References Cited

U.S. PATENT DOCUMENTS 4,013,702 3/1977 Cartier et al. .
5,239,106 8/1993 Shafer .................... 558/274

FOREIGN PATENT DOCUMENTS

| | | |
|---|---|---|
| 0218545 | 4/1987 | European Pat. Off. . |
| 0521499 | 1/1993 | European Pat. Off. . |
| 0636620 | 2/1995 | European Pat. Off. . |
| 1096936 | 2/1966 | United Kingdom . |

OTHER PUBLICATIONS

Fraktionierte Kristallisation, Sulzer Chemtech (Aug., 1992).

Primary Examiner—Johann Richter
Assistant Examiner—Michael G. Ambrose
Attorney, Agent, or Firm—Connolly & Hutz

[57] ABSTRACT

This invention provides a process for the purification of diphenyl carbonate (DPC) from crude products of diphenyl carbonate production. In this process, crude products are used that have a distillable fraction consisting of over 70 wt. % diphenyl carbonate and are fractionally crystallised from the melt (fractionating melt crystallisation).

2 Claims, No Drawings

PROCESS FOR THE PURIFICATION OF DIPHENYL CARBONATE

This invention provides a process for the purification of diphenyl carbonate (DPC) from crude products of diphenyl carbonate production, in which process crude products are used which have a distillable fraction consisting of over 70 wt. % diphenyl carbonate and they are fractionally crystallised from the melt (fractionating melt crystallisation).

Diphenyl carbonate may, for example, be produced by reacting phenol with phosgene in the presence of equimolar quantities of aqueous sodium hydroxide solution, by phosgenating phenol in the presence of catalyst, by transesterification of phenol with dimethyl carbonate or oxidative carbonylation of phenol.

Diphenyl carbonate may be produced and purified by distillation, extraction of phenol with water or by crystallisation (GB-A 1 096 936, U.S. Pat. No. 4,013,702, U.S. Pat. No. 5,239,106).

A crystallisation process is described, for example, in U.S. Pat. No. 5,239,106. This process exhibits various disadvantages:

Since it is not pure diphenyl carbonate, but an adduct with phenol, which is obtained from crystallisation, the crystallised product must be purified by distillation in a further processing stage. This process may only be used to work up crude mixtures having a low solids content, i.e. a low diphenyl carbonate content, because the mixtures are otherwise impossible to handle.

The educt material for crystallisation may thus only have a diphenyl carbonate content of less than 70 wt. %, preferably of no more than 50 wt. % (loc. cit., column 2, lines 40 to 53 and example 5), so that the crystal slurry may still be sufficiently separated from the mother liquor by filtration.

This is all the more disadvantageous as present-day industrial syntheses yield crude products which have distinctly higher diphenyl carbonate contents.

A process has now been found for the purification of diphenyl carbonate (DPC) from crude products of diphenyl carbonate production which have elevated diphenyl carbonate contents of above 70 wt. %, relative to the distillable fraction, by fractional melt crystallisation. Surprisingly, the process according to the invention is suitable for the purification of diphenyl carbonate crude products from various production processes, although these contain impurities and by-products of an entirely different nature.

The present invention provides a process for the purification of diphenyl carbonate by crystallisation from crude products of diphenyl carbonate production which have elevated diphenyl carbonate contents of above 70 wt. %, relative to the distillable fraction, by fractionating melt crystallisation, characterised in that the melt to be purified is cooled in the range from 85° to 45° C., preferably from 80° to 48° C., at a cooling rate of 20° to 0.1° C./h, preferably of 10° to 0.5° C./h, a holding time of 0 to 100 minutes, preferably of 1 to 70 minutes, is maintained at the lowest coolant temperature before separation of the residual melt, the crystallised product is then melted by heating at a heating rate of 20 to 0.1° C./h, preferably of 10° to 0.5° C./h, to a final temperature of 70° to 80° C., preferably of 72° to 79.5° C. and, during heating, further fractions of the melt with impurities are separated at pauses or without interruption of heating from the pure DPC melt arising at a higher temperature.

The process according to the invention may be used for the purification of diphenyl carbonate crude products from the processes listed below.

In the phase interface phosgenation of phenol, a crude product is produced containing over 99 wt. % DPC, which contains chloroformic acid phenyl ester as by-product.

A diphenyl carbonate crude product containing >95 wt. % DPC is obtained from the direct catalytic phosgenation of phenol. Here too, chloroformic acid phenyl ester and salicylic acid phenyl ester are produced as by-products.

Transesterification of dimethyl carbonate (DMC) with phenol yields, for example, reaction products containing 0 to 2 wt. % DMC, 1.5 to 10 wt. % phenol, 1 to 20 wt. % methylphenyl carbonate (MPC), 70 to 98 wt. % diphenyl carbonate and ppm concentrations of by-products such as salicylic acid phenyl ester, salicylic acid methyl ester and anisole. This mixture additionally optionally contains catalysts or residues thereof, i.e. titanium or tin compounds.

Depending upon the reaction conditions, running times and catalyst concentrations, oxidative carbonylation of phenol yields DPC crude solutions containing 20 to 90 wt. % phenol, 10 to 80 wt. % DPC and, additionally, low concentrations of by-products such as salicylic acid phenyl ester, o-phenylphenol and diphenyl ether. These mixtures additionally still contain components of the catalyst system, i.e. for example tetrabutylammonium bromide, sodium phenolate, manganese, Co or Cu and palladium compounds.

Crude solutions containing 70 to 85 wt. % DPC, with which the purification processes according to the invention may advantageously be performed, may also be obtained from the dilute solutions of this process by distilling off the phenol or by simple precrystallisation.

The quantity of diphenyl carbonate in the distillable fraction of the crude product is thus above 70 wt. %, preferably above 75 wt. %, particularly preferably above 80 wt. %.

The products obtained from the crystallisation according to the invention may be handled without problems; they are not phenol/diphenyl carbonate adducts and consequently need not be transformed into the pure diphenyl carbonate by additional distillation.

The process according to the invention of fractionating melt crystallisation of impure diphenyl carbonate may be performed both discontinuously and continuously as a single or multiple stage process.

The purification of diphenyl carbonate according to the invention may be performed using crystallisation processes as are, for example, described in Chem. Ing. Techn. 57 (1985), 91, Chem. Ing. Techn. 63 (1991), 881, Ullmann's Encyclopedia, 4th edition, volume 2, page 672 et seq. and 5th edition, volume 32, pages 3 et seq. or in the fractional crystallisation product literature from the company Sulzer dated August 1992.

Static and dynamic suspension and film crystallisation processes, preferably dynamic processes, may be used to purify diphenyl carbonate.

The process according to the invention may, for example, be performed in multi-tube crystallisers or modified plate-type heat exchangers of various designs with or without recirculation of the melt, with and without using pulsations or with and without subdivision of the tubes into segments with separate discharge. Falling film crystallisers of various designs, for example those known from EP-A 218 545, may also be used. Further apparatus which may be used comprises bubble column crystallisers, crystallising rolls and belts. Further details concerning continuously operating, suitable crystallisation devices may be found in EP-A 521 499.

Multi-tube crystallisers, plate-type heat exchangers of various designs with and without recirculation of the melt or falling film crystallisers are preferably used for the process according to the invention.

The crystallisation operation in the process according to the invention for purification of a diphenyl carbonate produced in accordance with the above-mentioned processes may be initiated both by spontaneous nucleation and by controlled addition of crystallisation nuclei (seeding). Crystallisation is preferably initiated by crystal nuclei.

The process according to the invention for obtaining purified diphenyl carbonate by melt crystallisation may be associated with purification processes involving distillation. It is thus possible, before using the melt crystallisation, in particular when separating diphenyl carbonate from reaction solutions optionally containing catalysts, to distil the diphenyl carbonate and subsequently to perform melt crystallisation according to the invention.

Moreover, on completion of crystallisation, it is also possible to remove small quantities of low-boiling constituents from the purified diphenyl carbonate by simple distillation.

Any catalysts present may largely be separated from the diphenyl carbonate by precipitation and filtration.

The process according to the invention may also be combined with other simple crystallisation processes, for example that described in U.S. Pat. No. 5,239,106, wherein mixtures are obtained which have already been concentrated in diphenyl carbonate, which are then further purified using the process according to the invention.

If the process according to the invention is performed in multi-tube crystallisers or plate-type heat exchangers, the melt to be purified is cooled in the range from 85° to 45° C., preferably from 80° to 48° C. at a cooling rate of 20° to 0.1° C./h, preferably of 10° to 0.5° C./h. During this cooling phase, the crystallisation operation is initiated by spontaneous nucleation or by controlled addition of nuclei (seeding), preferably by seeding. At the lowest temperature of the coolant, a holding time of up to 100 minutes is optionally maintained before separation of the residual melt. In both variants, the holding time is 0 to 100 minutes, preferably 1 to 70 minutes. The residual melt is then separated and the crystallised product is further purified by heating at a heating rate of 20° to 0.1° C./h, preferably of 10° to 0.5° C./h, to a final temperature of 70° to 80° C., preferably of 72° to 79.5° C.

In order to improve the effectiveness of purification, further pauses may act during this heating phase to separate further melt fractions and impurities melted prior to theses pauses may be removed together with the melt. In another embodiment, the initially occurring melt with the remaining exuded impurities may be separated during the heating operation without interruption of heating and are thus be separated from the pure DPC melt which arises at a higher temperature.

The diphenyl carbonate purified according to the invention may be used, for example, for the production of transesterification products such as polycarbonates (for example from bisphenol A).

EXAMPLES

Fractionating melt crystallisation operations are performed in the following examples. The produced diphenyl carbonate melt is introduced into a vertical, jacketed tube 150 cm in height and with an internal diameter of approximately 3 cm and, starting from 80° to 85° C., is cooled in accordance with a certain cooling rate (° C./h). The melt is then seeded with diphenyl carbonate crystals. Once a layer of crystals has formed, the residual melt is drained away and "sweating" of the crystals is then begun by heating at a certain rate, wherein further melt drips out. This operation is terminated at a temperature of 45° to 70° C., heating is then continued, the crystals remaining in the tube are melted and this purified diphenyl carbonate melt is collected in a separate vessel.

Example 1

A reaction product arising from transesterification of phenol with dimethyl carbonate and containing approximately 1 wt. % dimethyl carbonate 5 wt. % methylphenyl carbonate 5 wt. % phenol 84 wt. % diphenyl carbonate 5 wt. % titanium tetraphenolate was changed into a composition of 94 wt. % diphenyl carbonate 6 wt. % titanium tetraphenolate by distilling off the more readily volatile components, was introduced into the tube crystalliser, initially maintained at 78.0° C. and then cooled at 2.0° C./h. At 76.8° C., the melt was seeded with some crystals of diphenyl carbonate. When the melt reached 70.2° C., it was discharged and the heating medium then reheated at 2° C./h. Once a temperature of 78.1° C. had been reached, the mass of crystals remaining in the tube was melted and collected separately. After this first crystallisation stage, the melt contained only 0.3 wt. % of catalyst at a crystallisation yield of 55% and only 330 ppm of catalyst after a second similar stage.

Example 2

The reaction product with the composition stated in example 1 was distilled off from the catalyst and introduced into crystallisation with a composition of approximately 89 wt. % diphenyl carbonate 5 wt. % methylphenyl carbonate 5 wt. % phenol 1 wt. % dimethyl carbonate 140 ppm phenyl salicylate.

Starting from 70° C., cooling was performed at 5° C./h. When the melt reached 51.0° C., it was discharged and reheating was then performed at 3° C./h. Once the discharging melt reached a temperature of 75.7° C., the crystal deposit remaining in the tube was melted and collected separately. This amounted to 55.2% of the introduced product and contained 98.65 wt. % diphenyl carbonate 0.61 wt. % methylphenyl carbonate 0.72 wt. % phenol 0.02 wt. % dimethyl carbonate phenyl salicylate (<10 ppm)

The small quantities of low-boiling constituents may readily be reduced to critical values of <0.02% by distillation.

Example 3

The reaction product with the composition stated in example 1 was cooled to 60° to 70° C. and the precipitated catalyst, titanium tetraphenolate, was removed by suction filtration.

A mixture was obtained with a composition of approximately

- 89 wt. % diphenyl carbonate
- 5 wt. % methylphenyl carbonate
- 5 wt. % phenol
- 1 wt. % dimethyl carbonate
- 0.01 wt. % titanium tetraphenolate
- 121 ppm phenyl salicylate which was introduced into crystallisation and cooled from 72.0° C. to 62.0° C. at a rate of 2° C./h. Once the mother liquor had drained away, the tube was reheated at 2° C./h until the discharging melt was at a temperature of 78.0° C. The crystallised product remaining in the tube was then melted and collected separately.

This amounted to 42% of the introduced quantity and contained

- 99.50 wt. % diphenyl carbonate
- 0.18 wt. % methylphenyl carbonate
- 0.31 wt. % phenol and
- 10 ppm titanium tetraphenolate.

The product purified in this manner is crystallised once more using the same process. A diphenyl carbonate is obtained with a purity of 99.98 wt. % which contains below <3 ppm of titanium tetraphenolate.

Example 4

Example 3 was repeated with the difference that the cooling rate from 70° C. to 50.9° C. was 5° C./h and the heating rate from 50.9° C. to 76.1° C. was 3° C./h, and that seeding was performed with diphenyl carbonate at 68.5° C. Once a melt temperature of 76.1° C. had been reached, the crystals remaining in the tube were melted and the melt collected separately. This amounted to 48.3 wt. % of the introduced material and contained

- 98.80 wt. % diphenyl carbonate
- 0.42 wt. % methylphenyl carbonate
- 0.81 wt. % phenol
- 0.02 wt. % dimethyl carbonate
- 13 ppm titanium tetraphenolate
- phenyl salicylate not detectable (<10 ppm)

Comparative Example 1

Example 4 of U.S. Pat. No. 5,239,106 was replicated:

The mixture of 54.1 wt. % diphenyl carbonate, 44.6 wt. % phenol and 1.3 wt. % phenyl salicylate was melted, homogenised and cooled from 100° C. to 44° C. within 60 minutes while being stirred, wherein a thick crystal slurry was produced. This was suction filtered through a sintered filter maintained at exactly 44° C. with a thermostat and very thoroughly squeezed out. Once the mother liquor had stopped dripping out, the crystals were weighed. 43.2 g of crystals were obtained. These were remelted to ensure homogeneity and a sample of the melt was analysed.

It consisted of 30.63 wt. % phenol
69.11 wt. % diphenyl carbonate
0.26 wt. % phenyl salicylate.

The process of U.S. Pat. No. 5,239,106 thus produces distinctly less favourable results.

Comparative Example 2

A product of the composition as described in U.S. Pat. No. 230,106 was cooled from 70° C. to 44° C. at a rate of 2° C./h in a tube crystalliser in a similar manner to example 4 and left at this temperature for 1 hour. The melt was then allowed to drain away completely and the crystals in the tube were finally transformed into a melt. This amounted to 36% of the quantity introduced and contained 65.1% diphenyl carbonate (44% of introduced quantity of diphenyl carbonate)
34.8% phenol
400 ppm phenyl salicylate.

It may be seen from the examples that:

using the process according to the invention, it is possible to handle even highly concentrated mixtures containing above 70 wt. % of diphenyl carbonate without problems and to purify them by crystallisation (examples 1 to 4).

even after single-stage crystallisation, very pure products are obtained (example 3).

subsequent distillation of phenol is not required.

by-products (phenyl salicylate) are removed to below the detection limit (examples 2 to 4; comparative examples 1 and 2).

even after single-stage crystallisation, catalysts are reduced to very low levels and to below the detection limit after two-stage crystallisation (example 3).

the yield of pure crystallised product is distinctly higher than according to the prior art (compare example 2 with comparative examples 1 and 2).

Example 5

A reaction solution from direct carbonylation of phenol with a composition of approximately

- 24 wt. % diphenyl carbonate
- 74 wt. % phenol
- 1.5 wt. % tetrabutylammonium bromide
- 0.4 wt. % sodium phenolate
- 0.1 wt. % manganese compound
- 200 ppm palladium compound together with approximately 150 ppm of by-products such as salicylic acid phenyl ester and o-ophenylphenol, was changed into a composition of

- 73.2 wt. % diphenyl carbonate
- 18.9 wt. % phenol
- 7.5 wt. % tetrabutylammonium bromide
- 0.4 wt. % sodium phenolate
- 76 ppm manganese compound
- 5 ppm palladium compound together with approximately 500 ppm of by-products such as salicylic acid phenyl ester and o-phenylphenol by firming out the solids and distilling off the phenol, was introduced into the tube crystalliser, initially maintained at a temperature of 70° C. and cooled at 2° C./h. Once the melt had reached 61° C., it was held at this temperature for 30 minutes, then discharged and the heating medium was then reheated at 2° C./h. Once a temperature of 79° C. had been reached, the mass of crystals remaining in the crystalliser melted and was collected separately. After this first crystallisation stage, it was of the following composition:

- 97.5 wt. % diphenyl carbonate
- 2.0 wt. % phenol
- 0.5 wt. % tetrabutylammonium bromide
- 6 ppm sodium phenolate.

Pd and Mn compounds were no longer detectable. By-products such as salicylic acid phenyl ester and o-phenylphenol were present at concentrations of <10 ppm. After a further identical crystallisation stage, the DPC content was >99.8 wt. %.

Example 6

A reaction solution from direct carbonylation of phenol with a composition of approximately 75 wt. % diphenyl carbonate
23 wt. % phenol 1.5 wt. % tetrabutylammonium bromide
0.4 wt. % sodium phenolate 0.1 wt. % manganese compound
200 ppm palladium compound together with approximately 210 ppm of by-products such as salicylic acid phenyl ester and o-phenylphenol, was changed into a composition of 75.8 wt. % diphenyl carbonate
23.3 wt. % phenol
0.7 wt. % tetrabutylammonium bromide
0.2 wt. % sodium phenolate
80 ppm manganese compound
6 ppm palladium compound by filtering out the solids, was introduced into the tube crystalliser, initially maintained at a temperature of 70° C. and cooled at 2° C./h. Once the melt had reached 61° C., it was discharged and the heating medium was then reheated at 2° C./h. Once a temperature of 79° C. had been reached, the mass of crystals remaining in the crystalliser melted and was collected separately. After this first crystallisation stage, it was of the following composition:

98.6 wt. % diphenyl carbonate
1.1 wt. % phenol
0.3 wt. % tetrabutylammonium bromide
4 ppm sodium phenolate.

Pd and Mn compounds were no longer detectable. By-products such as salicylic acid phenyl ester and o-phenylphenol were present at concentrations of <8 ppm. The crystallisation product obtained in this manner was distilled and then had a DPC content of >99.9 wt. %.

Example 7

A reaction product from the catalytic phosgenation of phenol containing 75.6 wt. % diphenyl carbonate
23.5 wt. % phenol
0.9 wt. % chloroformic acid phenyl ester
1090 ppm salicylic acid phenyl ester was crystallised in a similar manner to example 2. In this manner, a purified diphenyl carbonate of the following composition was obtained:

99.5 wt. % diphenyl carbonate
0.5 wt. % phenol
<0.01 wt. % chloroformic acid phenyl ester
50 ppm salicylic acid phenyl ester.

The remaining quantities of low-boiling constituents could be removed to below the detection limit by simple distillation.

We claim:

1. A process for the purification of diphenyl carbonate by crystallization from crude products of diphenyl carbonate production which have elevated d-phenyl carbonate contents of above 70 wt. %, relative to the distillable fraction, by fractionating melt crystallization, comprising cooling the melt to be purified in the range from 85° to 45° C. at a cooling rate of 20° to 0.1° C./h, a holding time of 0 to 100 minutes, and is maintained at the lowest coolant temperature before separation of the residual melt, and the crystallized product is then melted by heating at a heating rate of 20° to 0.1° C./h to a final temperature of 70° to 80° C. and, during heating, further fractions of the melt with impurities are separated at pauses or without interruption of heating from the pure diphenyl carbonate melt arising at a higher temperature.

2. The process of claim 1, wherein the melt to be purified is cooled in the range from 80° to 48° C., at a cooling rate of 10° to 0.5° C./h, at a holding time of 1 to 70 minutes, and wherein the crystallized product is melted by heating at a heating rate of 10 to 0.5° C./h to a final temperature of 72° to 79.5° C.

* * * * *